United States Patent [19]

Fowles et al.

[11] 4,378,891
[45] Apr. 5, 1983

[54] BOTTLE CLOSURE

[75] Inventors: Thomas A. Fowles, McHenry; Glenn L. Slater, Ingleside, both of Ill.; David A. Winchell, Twin Lakes, Wis.

[73] Assignee: Baxter Travenol Laboratories, Inc., Deerfield, Ill.

[21] Appl. No.: 306,604

[22] Filed: Sep. 29, 1981

[51] Int. Cl.³ .............................................. B65D 1/02
[52] U.S. Cl. ..................................................... 215/32
[58] Field of Search ........................... 215/32, 33, 251

[56] References Cited

U.S. PATENT DOCUMENTS

| | | | |
|---|---|---|---|
| 2,372,181 | 3/1945 | Barr | 215/33 |
| 3,919,374 | 11/1975 | Komondowski | 264/515 |
| 4,093,093 | 6/1978 | Fowles et al. | 215/251 |
| 4,176,755 | 12/1979 | Winchell | 215/32 |
| 4,226,334 | 10/1980 | Weiler et al. | 215/355 |
| 4,319,701 | 3/1982 | Cambio | 222/541 |

Primary Examiner—Donald F. Norton
Attorney, Agent, or Firm—John P. Kirby, Jr.; Bradford R. L. Price; Gary W. McFarron

[57] ABSTRACT

A one-piece integral plastic container is disclosed which has an outer closure or overcap removable along a frangible line of weakness, and a separately-formed inner closure that is maintained in sterile condition by the outer closure until the container contents are dispensed. The inner closure comprises a tubular member inserted in fluid-tight relationship within the container neck after the container body and neck are molded, but prior to formation of the outer closure. The tubular member thus provides the dispensing outlet for the container and is maintained in sterile condition by the overcap which encloses it.

6 Claims, 3 Drawing Figures

BOTTLE CLOSURE

The present invention relates, in general, to plastic containers having a primary inner closure and an outer closure or overcap. More particularly, the present invention relates to the provision of a primary inner closure within a hermetically sealed container of one-piece integral construction.

One-piece, integral plastic containers of the type which are formed, filled and sealed in a single sterile operation have been satisfactorily used in a number of applications for storing and dispensing medical liquids, such as a sterile water, saline solution and the like. Examples of such containers may be found in U.S. Pat Nos. 4,176,755 to Winchell and 3,730,372 or 3,804,282 to Kemendowski.

These containers are typically opened by turning a plastic jacking ring which is threaded onto the container neck or top. Rotation of the jacking ring exerts an axial force, either in compression or in tension, on the top of the container and breaks the top off along a frangible line of weakness which is formed during the molding process.

Although such containers offer all of the inherent advantages of a one-piece hermetically sealed construction which is formed, filled and sealed in a continuous sterile operation, in some medical applications a container is preferred which has a sterile primary or inner closure and an outer protective closure or overcap. One such container is depicted in U.S. Pat. No. 4,093,093 to Fowles and Winchell. The container there has an open neck which is closed by a threaded interior cap. A plastic overcap which is melt sealed to the container maintains the entire inner closure, including the neck threads as well as the dispensing orifice and the pouring lip therearound, in sterile condition until the container is opened.

In a one-piece integral container, unlike the dual-closure system described above, the threads surrounding the dispensing orifice are on the outside of the container and may not be in perfectly sterile condition. Thus, such a container cannot be used in those medical applications where thread and pouring lip sterility are preferred. Accordingly, it is an object of the present invention to provide a container closure and method for making same, wherein the advantages of a one-piece, formed, filled and sealed container are obtained, while simultaneously providing a separate primary interior closure which may be maintained in a sterile environment until the container is opened for dispensing the contents.

It is a further object of the present invention to provide such a container which requires minimum changes to apparatus currently available for forming, filling and sealing one-piece containers.

These and other objects and features of the present invention are set forth in the following description of the preferred embodiment illustrated in the attached drawings, of which:

Figure 1:
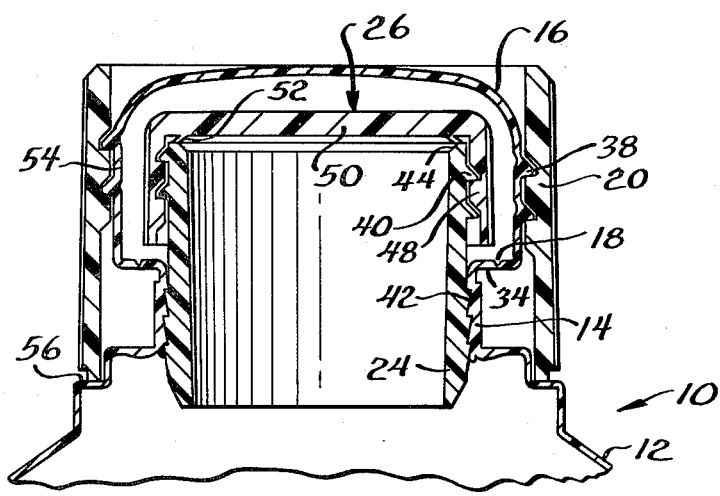
FIG. 1 is a fragmentary vertical cross-sectioned view of a container embodying the present invention.

In summary, the present invention is embodied in a one-piece, hermetically sealed container, generally at 10, which has a body 12, a neck 14, and a top 16 closing the neck. A frangible line of weakness 18 between the top and neck permits removal of the top by rotation of a threaded jacking ring 20. In accordance with the present invention, during the molding of the container 10, after the body and at least a portion of the neck have been formed between mold halves 22, but before the top is closed, a separately-formed tubular member 24 is force fit into fluid-tight relationship within the neck 14, thereby providing the dispensing outlet for the container. The upper end of the tubular member is closed by a primary closure cap 26. After insertion of the tubular member and closure cap, the top 16 is formed by another pair of movable molds 28, thereby sealing over and enclosing the primary closure in a sterile, hermetically sealed environment.

Figure 3:
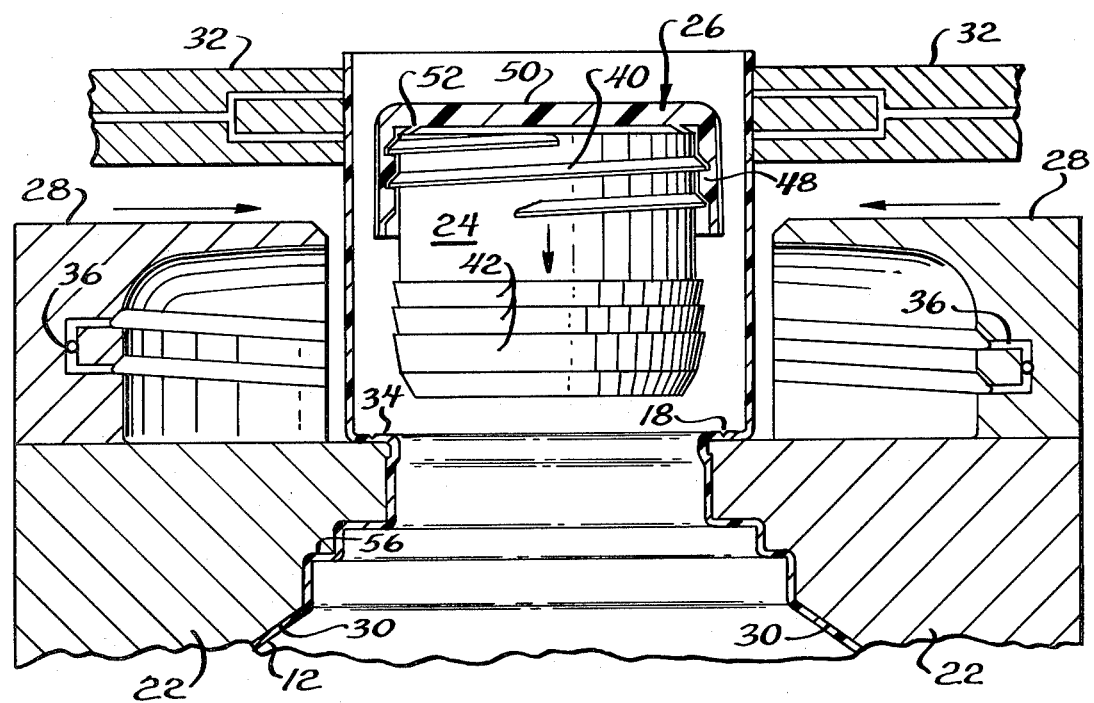
FIG. 3 is a fragmentary vertical cross-sectional view of the apparatus employed in making a container embodying the present invention.
Figure 2:
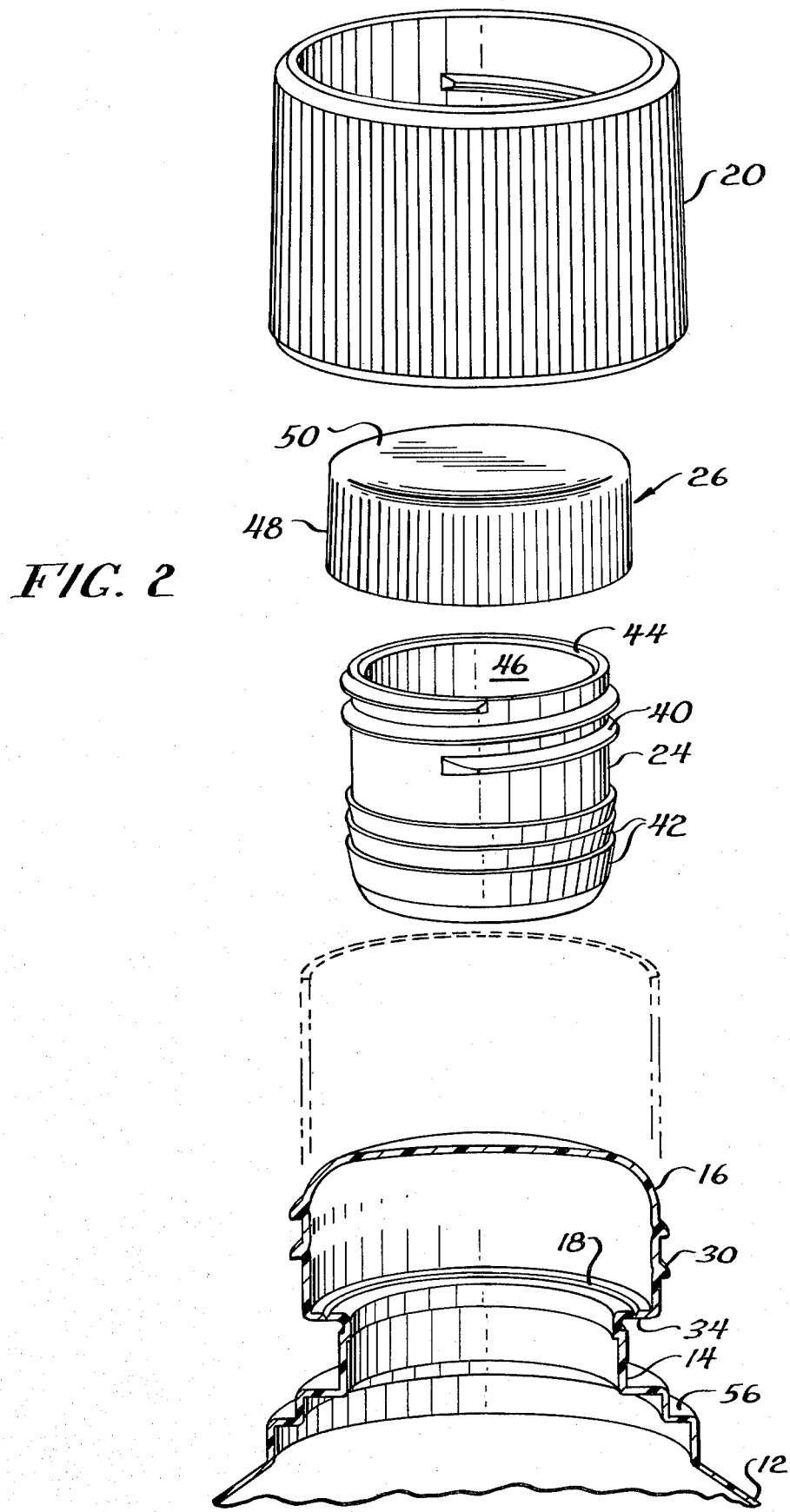
FIG. 2 is an exploded view, partially in section, of a container embodying the present invention, with the dashed lines depicting the outer closure of the container prior to sealing.

Turning now to a more detailed description of the preferred embodiment of the present invention, container 10 contains sterile medical liquid, such as sterile water, saline solution and the like, commonly supplied to hospitals. The container is preferably made of rigid polypropylene, polyethylene or other plastic material suitable for use with medical liquids. Referring briefly to FIG. 3, and to U.S. Pat. No. Re. 27,155 to Hansen, which is incorporated by reference herein, the container 10 is formed by extruding a plastic parison between the pair of movable mold halves 22. The mold halves 22 have interior cavity-forming surfaces 30 which define the shape of the container body 12 and at least a portion of the container neck 14.

When the mold halves 22 close about the parison, the upper end of the parison is held open by vacuum jaws 32. A filling mandrel (not shown), such as that depicted in U.S. Pat. No. 3,597,793 to Weiler et al., is then inserted into the upper end of the parison. The filling mandrel forces the contents of the container into the parison, simultaneously expanding the parison to conform to the mold cavity and filling the container. The mandrel may also simultaneously form the thin line of weakness 18 in a horizontal shoulder 34 of the container, above the neck.

The top 16 of the container 10 is formed by the separate pair of movable molds 24 which close against the upper portion of the parison, sealing the upper end of the container. These mold halves may also include vacuum ports 36 for drawing the parison into close conforming position with the surface of the molds, thus assuring that the top 16 will have the desired shape as well as proper formation of thread 38. These various features and operations are described herein briefly to orient the reader; additional details are set forth in the patents cited above.

In accordance with one aspect of the present invention, an inner primary closure is provided by inserting the tubular member 24 and primary closure cap 26 into the neck 14 of the container prior to formation of the top 16. The tubular member is preferably made of rigid plastic material such as polypropylene or polyethylene. Although it is understood that the container and tubular element need not be of the same material, usage of the same material may be preferred. The tubular element 24 is generally cylincrical, employing threads 40 at the upper end to receive the primary closure cap 26 and a plurality of annular sawtooth notches 42 at the lower end for tightly engaging the plastic wall of the neck. The upper end of the tubular element 24 terminates in a pouring lip 44 which defines and surrounds the dispensing orifice 46 for the contents of the container.

The primary closure cap 26 is also of pre-formed rigid plastic construction, and has a generally cylindrical, internally threaded side wall 48 and top wall 50. A flexible sealing ring 52 is located on the underside of the top wall to engage the upper end of the tubular element and seal against any leakage into the threaded area.

The pre-formed tubular element 24, with the closure cap 26 attached, is force fit into the container neck 14 during the molding of the container. Referring to FIG. 3, the tubular element is inserted after the container body 12 and at least a portion of the container neck 14 have been formed. At that point in time, the container neck would have cooled substantially by reason of heat conduction into the molds 22 and the filling of the container body with liquid. Nonetheless, the plastic is still sufficiently soft to receive the serrated end of the tubular element in close fitting, fluid tight contact, and the plastic is sufficiently soft to flow around the sawtooth notches forming the serrated surface to retain the tubular element against withdrawal. Of course, the tubular element is sized for tight fitting insertion into the container neck. In other words, the outermost diameter of the serrated edges may be slightly larger than the inside diameter of the neck, so as to form the tight fitting relationship therewith.

During the insertion of the tubular element 24, the parison is held open by vacuum jaws 32. After the insertion is complete, the top-forming molds 28 close about the upper end of the parison, pinching it together, and hermetically sealing the container and interior closure therewithin. During this operation, the inside of the parison is continuously flushed with sterile air, and other precautions, such as ultraviolet light, have been taken to insure the sterility of the contents. Because of protection from the overcap, the inner closure, including the tubular member 24, its threads 40, pouring lip 44 and closure cap 26, are maintained in sterile condition until the top 16 is removed to access the contents of the container.

Although the top of the container may take a variety of shapes, it is preferred that the top form an overcap with respect to the inner closure cap 26 so that the inner cap is easily accessed when the top is removed.

For removal, the top has a generally cylindrical threaded side wall 54 for receipt of the cylindrical, internally threaded jacking ring 20, which is likewise made of rigid plastic material. An annular shoulder 56 is provided on the container to engage the bottom edge of the jacking ring when it is rotated downwardly. Accordingly, downward rotation of the jacking ring exerts an upward axial force on the top of the container sufficient to break the frangible line of weakness 18 and thereby opening the container for access to the sterile primary inner closure.

Although the present invention has been described in terms of the preferred embodiment, it is understood that various modifications and substitutions may be made by those skilled in the art without departing from the scope of the present invention, as set forth in the following claims.

I claim:

1. In a hermetically sealed plastic container having a neck, a top integrally formed with the neck, a frangible line of weakness defined between the neck and top and a threaded jacking ring operable upon rotation to exert axial force on the top to sever it from the neck along the line of weakness, the improvement comprising, in combination:

a separately-formed closure interior of said container, said closure comprising a tubular member retained in fluid-tight position within the neck and defining a dispensing outlet for the container, and means normally closing said dispensing outlet, whereby said interior closure may be maintained in sterile condition within the hermetically sealed plastic container until the top thereof is removed for dispensing.

2. A container in accordance with claim 1 wherein said tubular member is sized for snug-fitting engagement within the container neck.

3. A container in accordance with claim 2 wherein said tubular member includes means for providing an interference fit with the container neck.

4. A container in accordance with claim 2 wherein the tubular member includes at least one annular retaining sawtooth on the exterior surface thereof to hold said tubular member in fluid-tight position within the container neck.

5. A container in accordance with claim 1 wherein the lower end of said tubular member is received within the container neck and the upper end defines said dispensing orifice.

6. A container in accordance with claim 5 wherein said upper end of said tubular member is threaded to receive a cap for closing said orifice.

* * * * *